United States Patent
Bruin et al.

(10) Patent No.: US 10,665,132 B2
(45) Date of Patent: May 26, 2020

(54) TRAINING DEVICE

(71) Applicant: Clement Clarke International Limited, Essex (GB)

(72) Inventors: Ronald John Bruin, Essex (GB); David William Spencer, Essex (GB); Mark Jeremy Sanders, Bedfordshire (GB)

(73) Assignee: CLEMENT CLARKE INTERNATIONAL LIMITED, Harlow (GB)

( * ) Notice: Subject to any disclaimer, the term of this patent is extended or adjusted under 35 U.S.C. 154(b) by 716 days.

(21) Appl. No.: 14/783,938

(22) PCT Filed: Apr. 11, 2014

(86) PCT No.: PCT/GB2014/051137
§ 371 (c)(1),
(2) Date: Oct. 12, 2015

(87) PCT Pub. No.: WO2014/167348
PCT Pub. Date: Oct. 16, 2014

(65) Prior Publication Data
US 2016/0049096 A1    Feb. 18, 2016

(30) Foreign Application Priority Data

Apr. 12, 2013 (GB) .................................. 1306709.5
Dec. 16, 2013 (GB) .................................. 1322175.9

(51) Int. Cl.
*G09B 23/28* (2006.01)
*A61M 15/00* (2006.01)
(Continued)

(52) U.S. Cl.
CPC ........... *G09B 23/28* (2013.01); *A61M 15/009* (2013.01); *A61M 15/0068* (2014.02);
(Continued)

(58) Field of Classification Search
CPC . G09B 23/28; A61M 15/0068; A61M 15/009; A63B 23/18; A63B 23/185
(Continued)

(56) References Cited

U.S. PATENT DOCUMENTS 1,133,713 A * 3/1915 Dressler .................. G10K 5/00
                                                    446/206
3,212,756 A * 10/1965 Hutton ...................... B06B 1/04
                                                    116/137 A
(Continued)

FOREIGN PATENT DOCUMENTS

FR        2763507        11/1998
GB        2372704         9/2002
(Continued)

OTHER PUBLICATIONS

Flo-Tone, http://web.archive.org/web/20120902060810/http://www.flo-tone.com, Sep. 2, 2012, Animation and Accompanying Explanation, accessed from the Internet Dec. 17, 2015, 1 page.
(Continued)

*Primary Examiner* — James B Hull
(74) *Attorney, Agent, or Firm* — Servilla Whitney LLC (57) ABSTRACT

The present invention provides a training device for training a user to use a pressurised metered dose inhaler (PMDI). The device comprises a body, air expulsion means (e.g. bellows) for expelling air along an air flow path and an actuator for actuation of the air expulsion means. The air flow path comprises a restriction such that upon expulsion of air along the air flow path, an audible signal is generated. The audible signal mimics that generated during use of a PMDI.

19 Claims, 6 Drawing Sheets

(51) Int. Cl.
*A63B 21/008* (2006.01)
*A63B 23/18* (2006.01)
*A63B 71/06* (2006.01)

(52) U.S. Cl.
CPC .......... *A63B 21/0087* (2013.01); *A63B 23/18* (2013.01); *A63B 23/185* (2013.01); *A61M 2205/071* (2013.01); *A61M 2205/183* (2013.01); *A61M 2205/43* (2013.01); *A61M 2205/581* (2013.01); *A61M 2205/583* (2013.01); *A63B 2071/0625* (2013.01); *A63B 2071/0694* (2013.01)

(58) Field of Classification Search
USPC ........................................................ 434/262
See application file for complete search history.

(56) References Cited

U.S. PATENT DOCUMENTS

| | | | | |
|---|---|---|---|---|
| 5,363,842 | A * | 11/1994 | Mishelevich | A61B 8/0875 |
| | | | | 128/200.14 |
| 5,447,150 | A | 9/1995 | Bacon et al. | |
| 5,758,638 | A * | 6/1998 | Kreamer | A61M 15/009 |
| | | | | 128/200.14 |
| 6,752,145 | B1 * | 6/2004 | Bonney | A61M 15/009 |
| | | | | 128/200.23 |
| 2002/0090601 | A1 | 7/2002 | Strupat et al. | |
| 2009/0139517 | A1 * | 6/2009 | Wachtel | A61M 15/0028 |
| | | | | 128/200.23 |
| 2011/0214597 | A1 * | 9/2011 | Foxcroft | G10K 5/00 |
| | | | | 116/137 R |

FOREIGN PATENT DOCUMENTS

| | | | |
|---|---|---|---|
| GB | 2490770 | 11/2012 | |
| WO | WO-9007351 A1 * | 7/1990 | ........ A61M 15/0065 |
| WO | WO-93/25258 | 12/1993 | |
| WO | WO-00/69496 | 11/2000 | |

OTHER PUBLICATIONS

Trainhaler Instructions, Clement Clarke International Ltd., http://www.clement-clarke.com/Portals/0/1905992-Trainhaler%201FU-4%20lang-pgs1-4.pdf May 2013, 2 pages.
United Kingdom Intellectual Property Office Search Report in GB1306709.5, dated Sep. 25, 2013, 6 pages.
United Kingdom Intellectual Property Office Search Report in GB1322175.9, dated Sep. 26, 2014, 4 pages.
PCT International Preliminary Report on Patentability in PCT/GB2014/051137, dated Oct. 13, 2015, 10 pages.
PCT International Search Report in PCT/GB2014/051137, dated Nov. 18, 2014, 7 pages.
PCT International Written Opinion in PCT/GB2014/051137, dated Nov. 18, 2014, 9 pages.

* cited by examiner

TRAINING DEVICE

CROSS-REFERENCE TO RELATED APPLICATIONS

This is the United States National Phase entry of International Application No. PCT/GB2014/051137, filed Apr. 11, 2014, which claims priority to GB 1306709.5, filed Apr. 12, 2013, and GB 1322175.9, filed Dec. 16, 2013, the disclosures of which are incorporated herein by reference in their entireties.

BACKGROUND

This invention relates to a training device for training a user to ensure the correct usage of a pressurised metered dose inhaler (PMDI). In particular, this invention relates to a training device which can be used in training in a way which mimics a PMDI.

Pressurised metered dose inhaler (PMDI) devices are the most popular and widely prescribed devices for respiratory drug delivery, with approximately 500 million manufactured each year.

In such devices, the active ingredient/drug is typically provided in the form of a solution or suspension held in a pressurised canister. Actuation of the canister is typically achieved by depressing the canister towards the body of the device. This causes an interaction between the canister and a valve seat that causes a metered dose to be ejected from the canister, along with a propellant gas (typically a hydrofluoroalkane (HFA) gas). The dose becomes aerosolized and available for inhalation by the patient.

The perception is that these devices are easy to use but this is far from the reality: seemingly simple steps such as coordination of actuation of the canister with inhalation, and inhaling at the appropriate flow rate are often performed incorrectly.

Correct use of PMDIs includes the following procedures: 1) breathing out gently (as far as comfortable); 2) sealing the mouth around the mouthpiece or spacer, breathing in slowly and steadily and then depressing the canister; and 3) continuing to breathe in slowly (preferably for at least 5 seconds) before removing PMDI from mouth.

Incorrect use of PMDIs has been shown to be very common in clinical practice. Numerous trials have demonstrated that a large percentage of patients (>60%) make errors in using PMDIs. Typical errors include depressing the canister before establishing the slow and steady inhalation, and not continuing to inhale for a sufficient length of time after depression of the canister.

When these errors occur, the medication is often not delivered as prescribed contributing to poor asthma control.

New users are typically given instructions on how to use a PMDI but written instructions alone have been found to be insufficient. Ideally, users should be trained in the correct usage of PMDIs (and preferably given revision-training to ensure that correct usage is maintained). It is known to use placebo PMDIs for instructional purposes and demonstration. Placebo PMDIs include a canister (containing propellant gas) in which the active ingredient has been omitted.

There are several known problems with the placebo devices. Firstly, they are not readily available—they are usually sourced through pharmaceutical companies. Secondly, they are costly to manufacture. These two problems can lead to the undesirable re-use of placebo devices in hospital/clinic settings across a significant number of patients (an MDI typically holds up to 200 actuations) despite recommendations for single patient use of both canister and mouthpiece. This, of course, raises concerns about hygiene.

Another problem with the placebo PMDIs is that the propellants used in the canisters have an environmental impact. For example, the propellants in PMDIs for asthma and chronic obstructive pulmonary disease represent approximately 40% of GSK's total carbon footprint. There is also some concern that the propellants may be a contributing factor in paradoxical bronchoconstriction.

A number of aids to help patients with their PMDI use do exist. There are various simple devices such as the 2-Tone Trainer™ (Canday Medical) and FLO-TONE™ pMDI attachment (Clement Clarke International) which provide an audible tone to indicate when the correct inspired air flow rate for drug delivery is achieved. However, the 2-Tone Trainer™ does not provide a realistic training experience since, although it has the appearance of a PMDI, it does not mimic the action of a PMDI and does not provide any training about the timing of canister TM depression. The FLO-TONE pMDI attachment is a spacer for attachment to a placebo or drug PMDI. Therefore it does not avoid the problems associated with the use of propellant gas, or the necessity to use a placebo or drug device during the teaching practice.

A number of more complex devices have also been proposed. These complex devices typically include computer hardware/software/electronics and thus are expensive and not suitable for home use. Some of these complex devices still require the use of a placebo PMDI and thus retain the problems mentioned above.

Accordingly, there remains the need for a training device for training users in the correct usage of a PMDI which is cost effective, suitable for home use, does not require the use of propellant gases, which can easily be cleaned and which can provide guidance on the coordination of inhalation and depression of the drug canister. The present invention aims to meet at least some of these needs.

SUMMARY OF THE INVENTION

In a first aspect, the present invention provides a training device for training a user to use a pressurised metered dose inhaler (PMDI), the device comprising:
 a body;
 air expulsion means for expelling air along an air flow path;
 an actuator for actuation of the air expulsion means;
 wherein the air flow path comprises a restriction such that upon expulsion of air along the air flow path, an audible signal is generated.

By providing a device having air expulsion means which is actuated using the actuator to force air along a restricted air flow path, it is possible to use air to generate an audible signal comparable to that generated during use of a PMDI. This allows for training of a user so that they can learn to coordinate their breathing with the actuation of the air expulsion means without the release of any environmentally-damaging propellant, without drug wastage and with the opportunity of convenient repeat practice.

In preferred embodiments, the actuator forms a sliding fit within the body and movement e.g. depression of the actuator into the body effects actuation of the air expulsion means.

By providing an actuator which is depressible into the body, the user can actuate the training device in the same manner as actuation of the PMDI (i.e. depression of the canister into the body of the PMDI). This provides a realistic training experience for the user so that as the user learns to coordinate their breathing with the actuation of the air expulsion means, they are effectively learning how to coordinate their breathing with the depression of a canister in a PMDI.

Preferably, the actuator comprises cooperation means for cooperating with the body to prevent rotational movement within the body and/or to prevent removal of the actuator from the body. The actuator cooperation means may comprise a ridge or groove which cooperates with a complementary groove or ridge inside the body for preventing rotational movement of the actuator within the body.

Preferably, the body has a tubular portion having an open upper end and a closed lower end. The tubular portion may have any cross-sectional profile. The tubular portion may have a circular cross-sectional profile (such that the tubular portion is a cylindrical portion). Alternatively, it may have a non-circular (e.g. oval) profile. In some embodiments, the device further comprises a body extension extending from the body at an angle (e.g. equal to or greater than 90 degrees and preferably between 90 and 100 degrees) relative to the axis of the tubular portion from proximal the closed lower end. The body extension is preferably a tubular extension having an open end distal the body.

By providing a device shaped like a PMDI, the user is able to obtain a realistic training experience. The body extension may be insertable into the user's mouth in a similar manner to an inhaler mouthpiece or it may be for connection to a spacer/cover which is for insertion into the user's mouth.

The body extension may be integral with the body or it may be a separate part which is connectable to and detachable/replaceable from the body. For example, the body extension may have connection means for releasably connecting with the body. The connection means may comprise one or more projections which is/are insertable into one or more respective recesses on the body, preferably on the tubular (e.g. cylindrical) portion of the body proximal the closed lower end. Alternatively, the connection means may comprise one or more recesses for receiving one or more respective projections provided on the body, preferably on the tubular (e.g. cylindrical) portion of the body proximal the closed lower end.

By providing a body extension which is a separate part which can be releasably attached to the body (so that the body resembles a PMDI), it is possible to remove the body extension after use (e.g. after insertion into a user's mouth). A new user can then affix another body extension for further use of the device. The body extension may be a single-use part i.e. it is discarded after use and detachment from the device. Alternatively it may be a multi-use part (preferably for multi-use by a single user) and it may be cleaned/disinfected after use and detachment from the device ready for re-attachment to the device at a later time.

In embodiments where the body extension is integral with the body, the device may further include a body extension cover for covering the body extension during use. The body extension cover can then be removed after use. A new user can then apply another body extension cover for further use of the device. The body extension cover may be a single-use part i.e. it is discarded after use and detachment from the device. Alternatively it may be a multi-use part (preferably for multi-use by a single user) and it may be cleaned/disinfected after use and detachment from the device ready for re-attachment to the device at a later time. The body extension cover preferably is adapted to cover the entire body extension.

The separate (replaceable) body extension and the body extension cover both serve to allow hygienic use of the device by multiple users in a clinic/hospital setting.

In some embodiments, the body does not have a body extension. It simply comprises the tubular (e.g. cylindrical) portion having an open upper end and a closed lower end. These embodiments may be inserted into an empty PMDI body (i.e. a PMDI containing no canister) with the closed lower end in abutment with the valve seat.

In these embodiments, a separate, replaceable body extension may be provided for fitting to the mouthpiece of the empty PMDI body. In this case, the connection means are for releaseably connecting with the expansion chamber/actuator nozzle region of the empty PMDI. For example, the connection means may comprise one or more projections which is/are insertable into one or more respective recesses provided adjacent the expansion chamber/actuator nozzle region on the empty PMDI body.

The body is preferably formed of plastics material e.g. polypropylene.

The actuator preferably comprises a tubular element having a closed upper end (upon which a user can press to actuate the air expulsion means) and an open or partially open lower end which is inserted into the open upper end of the tubular portion of the body. The tubular element may have any cross-sectional profile. It may have a circular cross-sectional profile (such that the tubular element is a cylindrical element). Alternatively, it may have a non-circular e.g. oval profile. Most preferably, the cross-sectional profile of the tubular element matches the cross-sectional profile of the tubular portion of the body (albeit having a smaller dimension).

In especially preferred embodiments, the tubular portion of the body is a cylindrical portion and the tubular element of the actuator is a cylindrical element and the lower end of the cylindrical element is inserted into the upper end of the cylindrical portion (the diameter of the actuator being less that the diameter of the cylindrical portion of the body).

The actuator is preferably formed of plastics material e.g. an acrylonitrile-butadiene-styrene (ABS) copolymer.

The actuator cooperation means may additionally or alternatively comprise an annular enlargement of at least part of the rim of the open lower end of the tubular (e.g. cylindrical) element of the actuator, the annular enlargement for cooperating with lugs on the inside of the walls of the tubular (e.g. cylindrical) portion of the body for preventing removal of the actuator from the body.

The air expulsion means may be housed inside the tubular (e.g. cylindrical) portion of the body or within the tubular (e.g. cylindrical) element of the actuator.

Preferably, the air expulsion means comprises a body which has a variable volume or comprises a body which has a variable volume portion such that, as the volume of the variable volume body/portion is reduced (by actuation of the air expulsion means e.g. by depression of the actuator), air is expelled from the variable volume body/portion along the air flow path.

The variable volume body/portion may have a wall portion which is deformable upon actuation (e.g. by depression of the actuator) to reduce the volume of the body/portion. The variable body/portion may be entirely defined by walls which are deformable upon actuation (e.g. by depression of the actuator) to reduce the volume of the body/portion. For example, the variable volume body/portion may have a flexible or corrugated wall portion or may be entirely defined by flexible or corrugated walls. Preferably, the deformable wall portion/walls are resilient such that they return to their original configuration after deformation. The action of returning to their original configuration preferably draws a reverse flow of air along the air flow path into the variable volume body/portion.

Preferably, the device comprises a resistance member for abutment with the variable volume body/portion so that upon actuation of the air expulsion means, the variable volume body/portion is pressed against the resistance member thus causing deformation of the deformable wall portion/deformable walls.

In a preferred embodiment, the body comprises a resistance member upstanding into the tubular (e.g. cylindrical) portion from the closed lower end. In an alternative embodiment, the actuator may comprise a resistance member upstanding into the tubular (e.g. cylindrical) element from the closed upper end. The resistance member may be, for example, a cylindrical or annular projection.

By providing a resistance member, depression of the actuator into the body is immediately met with resistance from the resistance member which causes the rapid reduction in the volume of the variable volume body/portion. Accordingly, the audible signal generated by the air escaping the variable volume body/portion along the restricted air flow path occurs almost simultaneously upon depression of the actuator as would be the case upon depression of the canister in a real PMDI.

In other embodiments, the resistance member may be omitted provided that the variable volume body/portion is in abutment with the inside of the closed lower end of the tubular (e.g. cylindrical) portion of the body. In this way, as the actuator is depressed into the body, the variable volume portion/body is pressed against the inside of the closed lower end to cause the rapid reduction in the volume of the variable volume body/portion.

In preferred embodiments, the air expulsion means comprises bellows. Most preferably, the air expulsion means comprises piston bellows having a cylindrical portion defined by corrugated walls and a closed end, the volume of the bellows cylindrical portion being reducible by compression of the corrugated walls upon actuation e.g. by depression of the actuator. Preferably, the corrugated walls are resilient such that they return to their original configuration after deformation. The action of returning to their original configuration preferably draws a reverse flow of air along the air flow path into the cylindrical portion of the bellows. The bellows are preferably formed of plastics material e.g. ethylene vinyl acetate (EVA) copolymer.

Preferably, the upstanding resistance member (e.g. at the closed end of the tubular (e.g. cylindrical) portion of the body/tubular (e.g. cylindrical) element of the actuator) or the closed lower end of the tubular (e.g. cylindrical) portion of the body is in abutment with the closed end of the piston bellows so that the audible signal generated by the air escaping the bellows through the restricted air flow path occurs almost simultaneously upon depression of the actuator.

Preferably the air flow path extends from the air expulsion means to an outlet port. Preferably, the restriction in the air flow path is proximal the outlet port so that any damping by the body and the actuator of the audible signal generated by the air as it passes through the restriction is minimised. The outlet port is preferably provided in the actuator (e.g. through the tubular (e.g. cylindrical) element) but may be provided in the body (e.g. through the tubular (e.g. cylindrical) portion). Where the outlet port is provided in the actuator and the actuator forms a sliding fit within the body, the outlet is positioned such that it remains exposed even when the actuator is depressed into the body. For example, the outlet port may be positioned proximal the closed upper end of the actuator. In some embodiments, a limiter (e.g. a ridge, lug or annular ring on the inside tubular (e.g. cylindrical) portion of the body or the outside of the tubular (e.g. cylindrical) element of the actuator) may be provided to limit the extent of depression of the actuator into the body.

In preferred embodiments, the air flow path further comprises a deflection proximal the restriction e.g. a right angled deflection. This has been found to increase the volume of the audible signal.

Preferably, the restriction in the air flow path is an orifice having a reduced cross-sectional area i.e. a smaller cross-sectional area than the air flow path preceding the restriction.

In preferred embodiments, the air flow path is at least partly defined by an insert. In preferred embodiments, the air expulsion means and actuator are connected by the insert and movement (e.g. depression of the actuator) is transferred directly to the air expulsion means through the insert. Preferably, the insert comprises a duct (which may be cylindrical or tapered) defining the air flow path from the air expulsion means to proximal the closed upper end of the actuator. The duct may be received in a seat provided on the inside of the closed upper end of the actuator. In alternative embodiments, the air expulsion means and body are connected by the insert. In these embodiments, the insert comprises a duct (which may be cylindrical or tapered) defining the air flow path from the air expulsion means to proximal the closed lower end of the body. The duct may be received in a seat provided on the inside of the closed lower end of the body.

In preferred embodiments, when the air flow path reaches the closed upper end of the actuator/closed lower end of the body, it is deflected through 90 degrees through an orifice in the duct, the orifice having a smaller cross-sectional area than the duct.

In preferred embodiments, the air flow path comprises a plurality of restrictions e.g. a plurality of orifices. Most preferably, the air flow path comprises an upstream orifice having a reduced cross-sectional area (i.e. a smaller cross-sectional area than the air flow path preceding the orifice) and a downstream orifice having larger cross-sectional area than the upstream orifice. The upstream orifice is closer to the air expulsion means than the downstream orifice.

By providing two orifices in the air flow path, it has been found that the smaller upstream orifice creates a high speed jet of air and then the larger downstream orifice creates a turbulent air flow which generates the audible signal.

Most preferably, the deflection in the air flow path occurs before and proximal the smaller upstream orifice.

In preferred embodiments, the insert connecting the air expulsion means and actuator or body defines both the upstream and downstream orifices. As discussed above, the insert preferably comprises a duct defining the air flow path from the air expulsion means to proximal the closed end of the actuator/body, the duct preferably being received in a seat provided on the inside of the closed end of the actuator/body. When the air flow path reaches the closed end of the actuator/body, it is deflected through 90 degrees though the upstream orifice in the duct, the upstream orifice having a smaller cross-sectional area than the duct. In preferred embodiments, the insert further comprises a flange extending from the duct and supporting an upstanding plate, the upstanding plate at least partially defining the downstream orifice which is in alignment with and spaced from the upstream orifice. The upstanding plate may extend to the closed end of the actuator/body or to a lug extending from the inside of the closed end of the actuator/body. The closed end of the actuator/body or the lug may partially define the upstream orifice. In some embodiments, the upstream orifice may be entirely defined by a lug depending from the inside surface of the closed end of the actuator/body.

To further increase the volume of the audible signal, a sound box is provided in the air flow path, preferably adjacent the outlet port. The air flow path passes through the sound box after passing through the restriction(s) and the sound box acts to amplify the audible signal generated.

In preferred embodiments, the sound box may be defined by the walls of the tubular (e.g. cylindrical) element of the actuator surrounding the outlet port, the closed upper end of the actuator, the flange depending from the duct of the insert (where the flange extends up to the walls of the tubular (e.g. cylindrical) element of the actuator) and by inner walls depending from the inside of the closed upper end of the tubular (e.g. cylindrical) element of the actuator, the inner walls extending downwards to the flange and across to the walls of the tubular (e.g. cylindrical) element of the actuator. If the upstream orifice is partly defined by a lug depending from the closed inside end of the actuator, the inner walls extend either side of the lug.

In other embodiments, the sound box may be defined by the walls of the tubular (e.g. cylindrical) portion of the body surrounding the outlet port, the closed lower end of the body, the flange depending from the duct of the insert (where the flange extends to the walls of tubular (e.g. cylindrical) portion of the body) and by inner walls depending from the inside of the closed lower end of the tubular (e.g. cylindrical) portion of the body, the inner walls extending upwards to the flange and across to the walls of the tubular (e.g. cylindrical) portion of the body. If the upstream orifice is partly defined by a lug depending from the closed inside end of the body, the inner walls extend either side of the lug.

In some embodiments, the device includes an inhalation flow path through the body to the body extension. This may extend from the open upper end of the tubular (e.g. cylindrical) portion of the body, through the body to the closed lower end of the tubular (e.g. cylindrical) portion of the body and to the body extension so that as a user encloses the open end of the body extension (or a spacer/body extension cover) in their mouth and inhales, they can mimic the inhalation technique that they would use with a PMDI. In alternative embodiments, the inhalation flow path may extend from an inhalation flow path inlet provided in the actuator and/or the body e.g. in the wall of the tubular (e.g. cylindrical) element and/or the tubular (e.g. cylindrical) portion. Preferably, the inhalation flow path inlet is provided in the tubular (e.g. cylindrical) portion proximal the closed lower end. In embodiments with an inhalation flow path through the body, the device is preferably provided with a replaceable body extension or an integral body extension with a body extension cover to avoid contamination of the device. In this way, the device can be used for training of more than one user, e.g. in a hospital or clinic setting.

In embodiments with an inhalation flow path through the body to the body extension, the body extension cover includes at least one orifice to allow inhalation by the user.

In some embodiments, there is no inhalation flow path between the body and body extension. Instead, a sealing plate is provided between the body extension and the tubular (e.g. cylindrical) portion of the body. In embodiments, where a replaceable body extension is provided, the sealing plate may form part of the body extension or it may form part of the body. Preferably, the sealing plate forms part of the detachable body extension with a rear surface of the sealing plate carrying the connection means. Preferably, the sealing plate has a smooth front surface which forms a smooth join with the body extension i.e. there are no abrupt deflections between the sealing plate and the walls of the body extension. In this way, the sealing plate and body extension can be thoroughly cleaned/disinfected between uses with no risk of dirt/germs getting trapped in surface irregularities or at joins.

In preferred embodiments, the training device is intended for use with a spacer (i.e. a chamber/tube) or body extension cover (as discussed above). The spacer/cover may have an attachment end for fitting onto the body extension e.g. onto the open end of the body extension.

In order to provide an inhalation flow path for embodiments comprising a sealing plate, one or more air inlets may be provided in the body extension and/or the spacer/cover. The air inlet(s) may also be provided in embodiments with no sealing plate to provide a further inhalation flow path. The spacer/cover may be provided with one or more air inlets through which air can be drawn as the user inhales. However, preferably, the body extension at least partly defines the one or more air inlets. It is possible to provide at least one air inlet defined entirely by the body extension (i.e. as an aperture through the walls of the body extension), but such an air inlet will be difficult to clean thus limiting re-use of the device by multiple users.

Accordingly, it is preferred to provide at least one air inlet which is defined partly by the body extension and partly by the spacer/cover (when attached) e.g. by the attachment end of the spacer/cover. To achieve this, at least one notch is provided in the body extension, the at least one notch extending from the open end of the body extension towards the body (and sealing plate if present). The dimensions of the/each notch are such that, when the spacer/cover is in place, at least one air inlet is defined by the notch and the attachment end of the spacer/cover. The notch can easily be cleaned after removal of the spacer/cover. Preferably, two opposing notches are provided in opposing walls of the body extension.

Most preferably, the body extension comprises a tubular extension extending from or attachable to the closed lower end of the tubular (e.g. cylindrical) portion of the body. Preferably, the tubular extension comprises a receiving portion with an open end distal the body for receiving the attachment end of the spacer/cover (e.g. in a press-fit arrangement). Preferably, the tubular extension comprises a connecting portion which abuts the receiving portion and the body. There is preferably a stepped join or a ridge between the receiving portion and the connecting portion which limits the extent to which the spacer/cover can be fitted onto the tubular extension so that the receiving portion may be enclosed within the spacer/cover but the connecting portion remains exposed. In other embodiments, there is an intermediate portion between the receiving portion and the connecting portion, the intermediate portion having a plurality of stop points (e.g. ridges, lugs or annular rings) for limiting the extent to which a spacer/cover can be fitted onto the intermediate section. In these embodiments, the receiving portion and at least part of the intermediate portion will be enclosed when a spacer/cover is attached but the connecting portion will remain exposed.

Preferably, the or each notch extends from the open end of the receiving portion and into the connecting portion (so that the air inlet is exposed when the spacer/cover is in situ). Most preferably, the or each notch extends from the open end of the receiving portion, across the stepped join/ridge or the intermediate portion, through the connecting portion to proximal the body (and the sealing plate if present).

Preferably, there are two such notches (and thus two air inlets), one either side of the tubular extension. Most preferably, the two notches/air inlets are in alignment either side of tubular extension.

Preferably, the size of the or each notch is selected such that, when a spacer/cover is in place, the size of the resulting air inlet(s) is such that the flow rate and back pressure in the inhalation flow path match the flow rate and back pressure present in typical PMDIs. For example, the total area of the air inlet(s) may be between 20 and 135 mm$^2$, preferably between 20 and 132 mm$^2$ and most preferably, around 20 mm$^2$, around 57 mm$^2$, around 61 mm$^2$, around 118 mm$^2$ or around 132 mm$^2$—these areas provide air flow rates and back pressure values which match five commonly used PMDIs. Preferably, there are two air inlets, preferably of equal size and each air inlet preferably has an area of between 10 mm$^2$ and 70 mm$^2$, preferably between 10 mm$^2$ and 66 mm$^2$ and most preferably around 10 mm$^2$, around 28 mm$^2$, around 30 mm$^2$, around 59 mm$^2$ or around 66 mm$^2$—these areas provide air flow rates and back pressure values which match five commonly used PMDIs. It should be noted that the area of the air inlet(s) is also equivalent to the area of the notch(es) in the connecting portion of the tubular extension for embodiments where there is no intermediate portion.

For embodiments where there is an intermediate portion, the size of the air inlet(s) discussed above are equivalent to the area of the notch(es) in the connecting portion combined with the area of the notch(es) from the connecting portion to the various stop points. The plurality of stop points allow the device to mimic the air flow/back pressure characteristics of a number of commonly used PMDIs.

For example, if two stop points are included in the intermediate portion (a first stop point proximal the connecting portion and a second stop point distal the receiving portion), two air inlet sizes can be achieved using the device. The smaller air inlet size (mimicking a high pressure drop PMDI) can be achieved by arranging the attachment end of the spacer/cover adjacent the first stop point. In this case, the preferred air inlet size is equivalent to the area of the notch(es) in the connecting portion combined with the area of the notch(es) between the connecting portion and the first stop point. The larger air inlet size (mimicking a lower pressure drop PMDI) can be achieved by arranging the attachment end of the spacer/cover adjacent the second stop point. In this case, the preferred air inlet size is equivalent to the area of the notch(es) in the connecting portion combined with the area of the notch(es) between the connecting portion and the second stop point. By way of example, the total air inlet size (and therefore the size of the notch(es)) defined by the connecting portion and intermediate portion between the connecting portion and the first stop point) may be selected from around 10 mm$^2$, around 28 mm$^2$, around 30 mm$^2$ or around 59 mm$^2$ and the total air inlet size (and therefore the size of the notch(es)) defined by the connecting portion and intermediate portion between the connecting portion and the second stop point) is larger and may be selected from around 28 mm$^2$, around 30 mm$^2$, around 59 mm$^2$ or around 66 mm$^2$.

A device having a body extension having an intermediate section with 5 stop points will be able to mimic the flow rate/back pressures of all five commonly used PMDIs.

In preferred embodiments with two air inlets either side of the body extension, the notches preferably extend to the sealing plate and the sealing plate is preferably provided with a deviator in alignment with the two air inlets. The deviator acts to prevent the two streams of the inhalation flow path entering through the two air inlets from buffeting each other and creating turbulence. The deviator may be, for example, a bump (e.g. a circular bump) or a ridge. The bump or ridge may have a height such that it protrudes from the sealing plate by an amount that is between ¼ and ½, preferably around ⅓ of the length of the connecting portion (i.e. from the sealing plate to receiving portion) of the tubular extension.

In preferred embodiments, the device further includes a counter for providing an indication of time elapsed since actuation of the air expulsion means. The counter may be a clockwork counter that provides an audible indication of time elapsed since actuation of the air expulsion means. For example, the counter may tick to provide an indication of seconds elapsed.

Alternatively, the counter may provide a visual indication of the time elapsed since actuation of the air expulsion means. For example, the counter may comprise a liquid-filled reservoir connected to a second air flow path, the second air flow path extending from the air expulsion means (e.g. the bellows) to a second outlet (e.g. in the actuator or body). The second outlet is either in direct fluid communication with the liquid-filled reservoir or the second outlet is connected to a plunger which is contained within (and seals) the liquid-filled reservoir. The liquid-filled reservoir is connected to an upstanding tube (preferably a capillary tube) which is visible to the user as they use the device. As the actuator is depressed into the tubular (e.g. cylindrical) portion of the body, air is expelled along the second air flow path to the second outlet and from there to the liquid-filled reservoir or to the plunger. The increased pressure in the reservoir (caused either directly or indirectly (via the plunger) as a result of air flow along the second air flow path) causes the liquid in the reservoir to rise within the upstanding tube. The viscosity of the liquid in the reservoir is selected such that, after rising within the tube, it recedes back into the reservoir at a predetermined rate. Preferably, the predetermined rate is such that it recedes back into the reservoir over a time period of around 5 seconds. A capillary tube is preferred as this emphasises and thus enhances the visibility of liquid movement within the tube. To provide the user with an indication of the time elapsed, the counter is preferably provided with a graduated display aligned with the (capillary) tube.

The counter provides an indication to the user of how long they are continuing or should continue to inhale after depression of the actuator/actuation of the air expulsion means. A user should continue to inhale for at least five seconds after hearing the audible signal generated by the device. In a preferred embodiment, the counter will indicate lapsed time for at least five seconds.

Preferably, the device of the present invention is for use with a spacer as described in GB2490770A and sold as a FLO-TONE pMDI attachment spacer by Clement Clarke International. This spacer includes a sound generator which generates an audible tone when the correct air flow rate for drug delivery is achieved.

Accordingly, the user affixes the attachment end of the spacer to the open end of the body extension and inhales until the tone indicating the correct flow rate is generated by the spacer. At that time, the user depresses the actuator to activate the air expulsion means. The air expulsion means acts to force air through the restricted air flow path thus generating an audible signal that is comparable to the sound generated by the propellant gases upon depression of a canister into the body of a PMDI. The user is then instructed to continue breathing in after hearing the audible signal generated by the device for as long as they can whilst maintaining the tone generated by the spacer. Preferably, the counter will tick to provide some indication of time elapsed and the user should aim to keep inhaling for at least five seconds after depression of the actuator/actuation of the air expulsion means. Accordingly, by using the device of the present invention, especially in combination with the FLO-TONE pMDI attachment spacer, a user can learn to use a PMDI correctly by undergoing a realistic training experience where the actions of using the device and the sounds generated by the device accurately mimic those of a PMDI.

Alternatively, the body extension itself (rather than the spacer) may comprise the sound generator which generates an audible tone when the correct air flow rate for drug delivery is achieved.

BRIEF DESCRIPTION OF DRAWINGS

A preferred embodiment of the present invention will now be described with reference to the accompanying Figures in which.

DETAILED DESCRIPTION OF PREFERRED EMBODIMENTS

FIGS. 1 to 5 show a first preferred embodiment of a training device for training a user to use a pressurised metered dose inhaler (PMDI). The Figures show the device in combination with a FLO-TONE pMDI attachment spacer.

Figure 4:
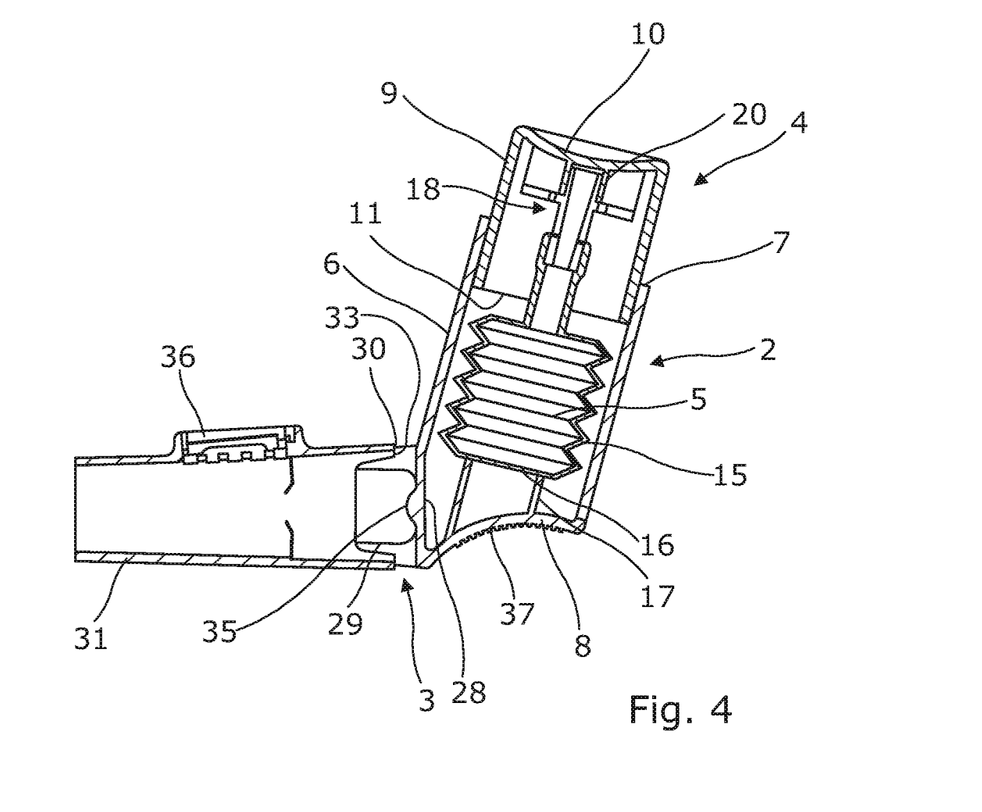
FIG. 4 shows a cross-sectional view along line A-A shown in FIG. 1.
Figure 5:
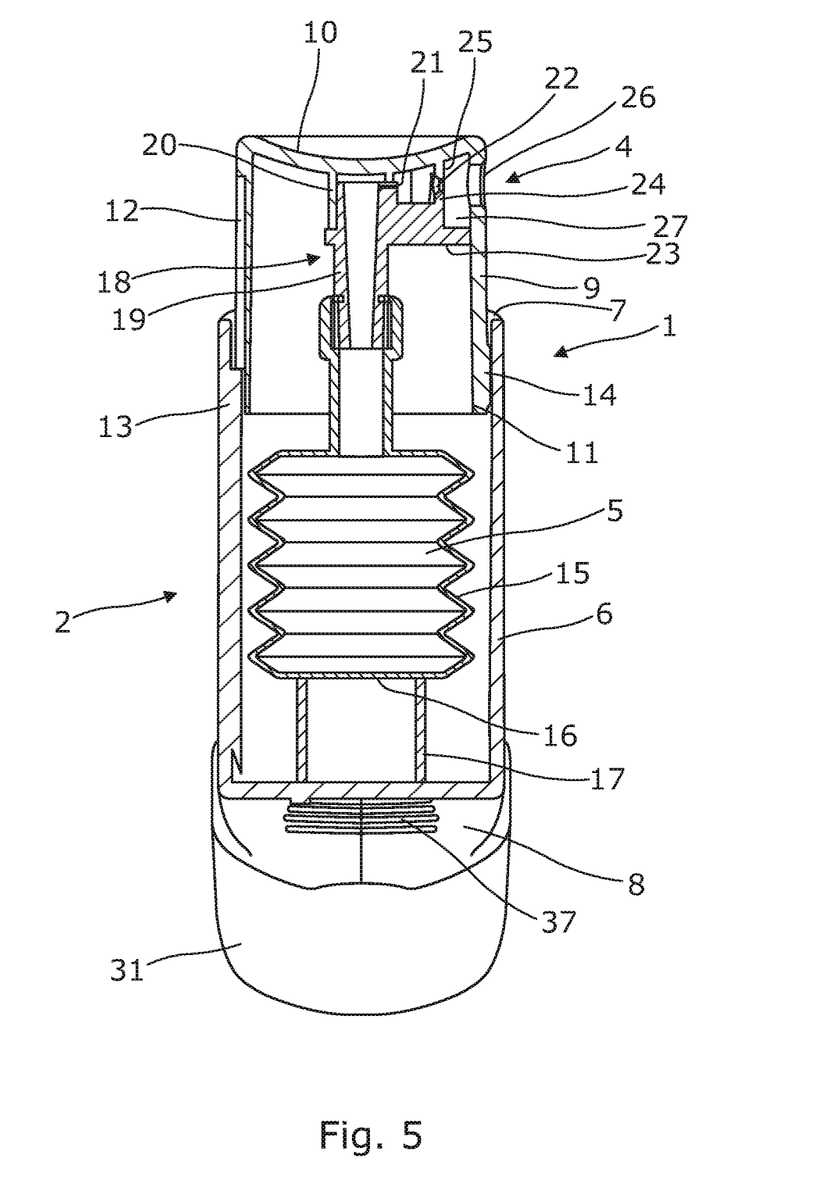
FIG. 5 shows a cross-sectional view along a line at ninety degrees to line A-A.

The device 1 comprises a body 2, an integral body extension 3 and an actuator 4 for actuation of air expulsion means 5 (shown in the cross-sectional views in FIGS. 4 and 5 and discussed further below).

The device 1 is shaped like a PMDI, the body 2 having a cylindrical portion 6 with an open upper end 7 and a closed lower end 8 and the body extension 3 extending at an angle (between 90 and 100 degrees) relative to the axis of the cylindrical portion 6 from proximal the closed lower end 8. The closed lower end 8 has a depression and a grip 37 for accommodating the user's thumb when the device is being held.

The actuator 4 comprises a cylindrical element 9 having a closed upper end 10 and an open lower end 11 which is inserted into the open upper end 7 of the cylindrical portion 6 of the body 2 (the diameter of the actuator 4 being less that the diameter of the cylindrical portion 6 of the body 2.)

The cylindrical element 9 forms a sliding fit within the cylindrical portion 6 of the body 2 and depression of the actuator 4 into the body 2 effects actuation of the air expulsion means 5. The closed upper end 10 of the actuator 4 includes a depression for receiving a user's finger for depression of the actuator 4 into the body 2.

The actuator 4 comprises cooperation means for cooperating with the body to prevent rotational movement within the body and/or to prevent removal of the actuator from the body. The actuator cooperation means comprises a groove 12 which cooperates with a complementary ridge 13 inside the body for preventing rotational movement of the actuator 4 within the body 2.

The actuator cooperation means additionally comprises an annular enlargement 14 of at least part of the rim of the open lower end 11 of the cylindrical element 9 of the actuator 4, the annular enlargement 14 for cooperating with lugs (not shown) on the inside of the walls of the cylindrical portion 6 of the body 2 for preventing removal of the actuator 4 from the body 2.

The air expulsion means 5 are for expelling air along an air flow path. The air expulsion means 5 comprises piston bellows having a cylindrical portion defined by corrugated walls 15 and a closed lower end 16. The volume of the cylindrical portion of the bellows is reducible by compression of the corrugated walls 15 upon actuation by depression of the actuator 4 into the body 2. As the volume of the bellows is decreased, air is expelled along the air flow path.

The body 2 comprises a resistance member 17 which is an annular projection upstanding into the cylindrical portion 6 from the closed end 8 of the cylindrical portion 6 for abutment with the closed lower end 16 of the piston bellows.

The air expulsion means 5 and actuator 4 are connected by an insert 18 and movement (i.e. depression of the actuator 4) is transferred directly to the air expulsion means 5 through the insert 18. The insert 18 comprises a duct 19 defining the air flow path from the air expulsion means 5 to proximal the closed upper end 10 of the actuator 4. The duct 19 is received in a seat 20 provided on the inside of the closed upper end 10 of the actuator 4.

When the air flow path reaches the closed upper end 10 of the actuator 4, it is deflected through 90 degrees through an orifice 21 in the duct 19, the orifice 21 having a smaller cross-sectional area than the duct 19. The orifice 21 constitutes a first (upstream) restriction in the air flow path.

The air flow path further includes a second (downstream) orifice 22, the second orifice 22 having larger cross-sectional area than the first upstream orifice 21. The upstream orifice 21 is closer to the air expulsion means 5 than the downstream orifice 22.

Upon expulsion of air (from the air expulsion means 5) along the air flow path, the smaller upstream orifice 21 creates a high speed jet of air and the larger downstream orifice 22 creates a turbulent air flow which generates an audible signal.

Both the upstream and downstream orifices 21, 22 are defined by the insert 18 connecting the air expulsion means 5 and actuator 4. The first (upstream) orifice is provided in the duct 19 of the insert just after the 90 degree deflection of the air flow path. The insert 18 comprises a flange 23 extending from the duct 19 and supporting an upstanding plate 24, the upstanding plate 24 partially defining the downstream orifice 22 which is in alignment with and spaced from the upstream orifice 21. The upstanding plate 24 extends to a lug 25 extending down from the inside of the closed upper end 10 of the actuator 4. The lug 25 partially defines the upstream orifice 22.

The air flow path extends from the air expulsion means 5 to an outlet port 26 in the actuator 4. The downstream orifice 22 is proximal the outlet port 26 so that any damping by the body 2 and the actuator 4 of the audible signal generated by the air as it passes through the downstream orifice 22 is minimised.

To further increase the volume of the audible signal, a sound box 27 is provided in the air flow path, adjacent the outlet port 26. The air flow path passes through the sound box 27 after passing through the orifices 21, 22 and the sound box 27 acts to amplify the audible signal generated.

The sound box 27 is defined by the walls of cylindrical element of the actuator 4 surrounding the outlet port 26, the closed upper end 10 of the actuator 4, the flange 23 depending from the duct 19 of the insert (where the flange 23 extends up to the walls of cylindrical element of the actuator 4) and by inner walls (not shown) depending from the inside of the closed upper end 10 of the cylindrical element of the actuator 4, the inner walls extending downwards to the flange 23 and across to the walls of the cylindrical element of the actuator 4. The inner walls extend either side of the lug 25 which at least partly defines the second, upstream orifice 22.

A sealing plate 28 (shown in FIG. 4) is provided between the body extension 3 and the cylindrical portion 6 of the body. The sealing plate 28 has a smooth surface and forms a smooth join with the body extension 3 i.e. there are no abrupt deflections between the sealing plate 28 and the walls of the body extension 3.

Figure 1:
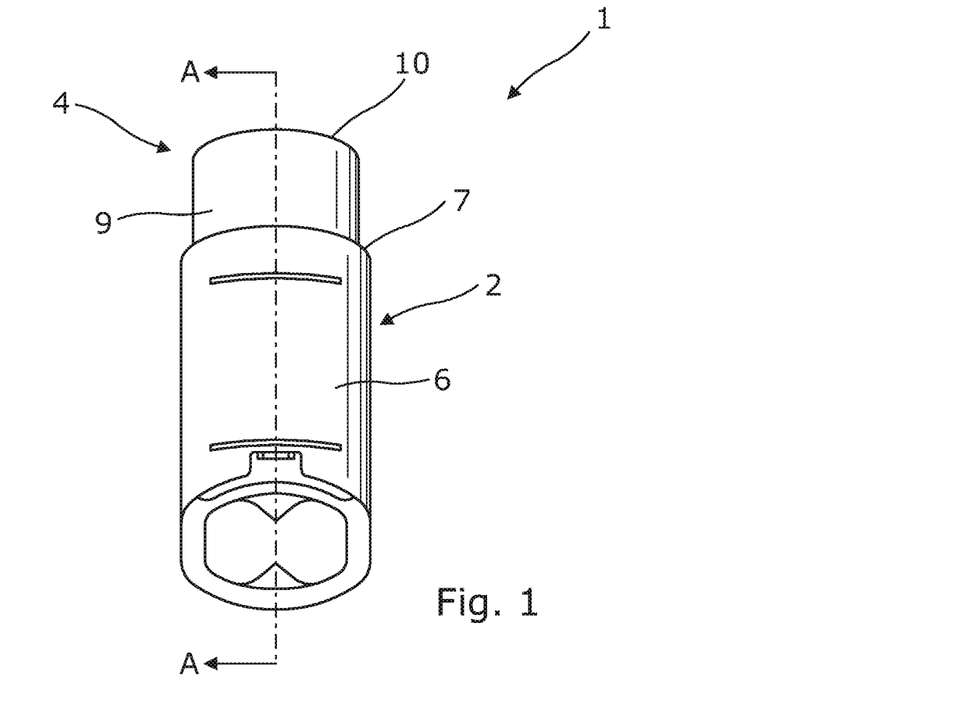
FIG. 1 shows a front view of the first embodiment of the present invention.
Figure 2:
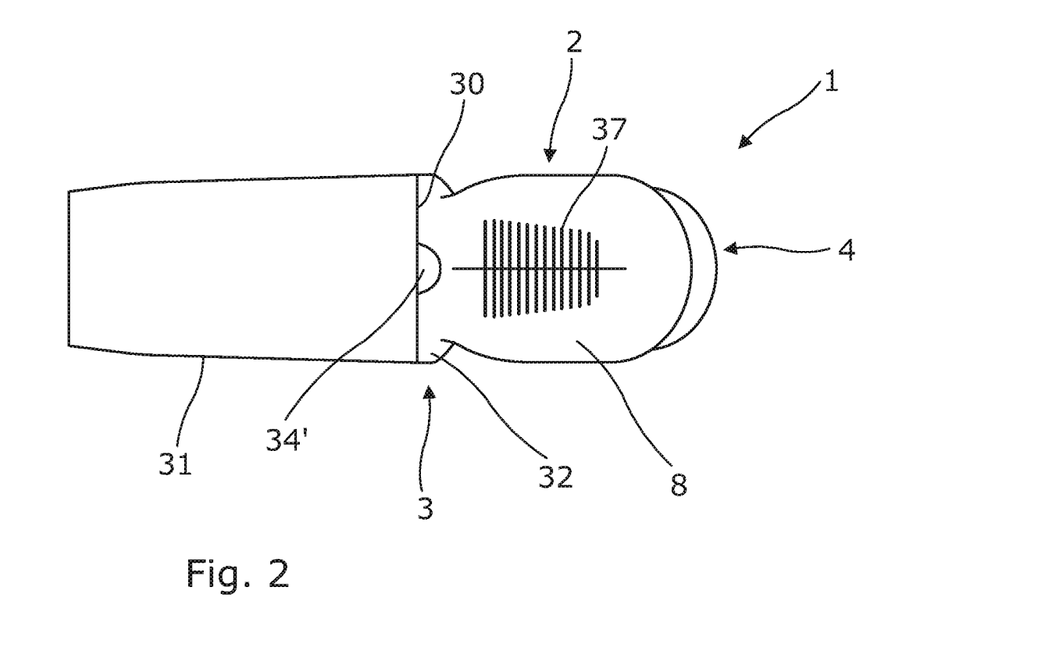
FIG. 2 shows a bottom view of the first embodiment of the present invention.
Figure 3:
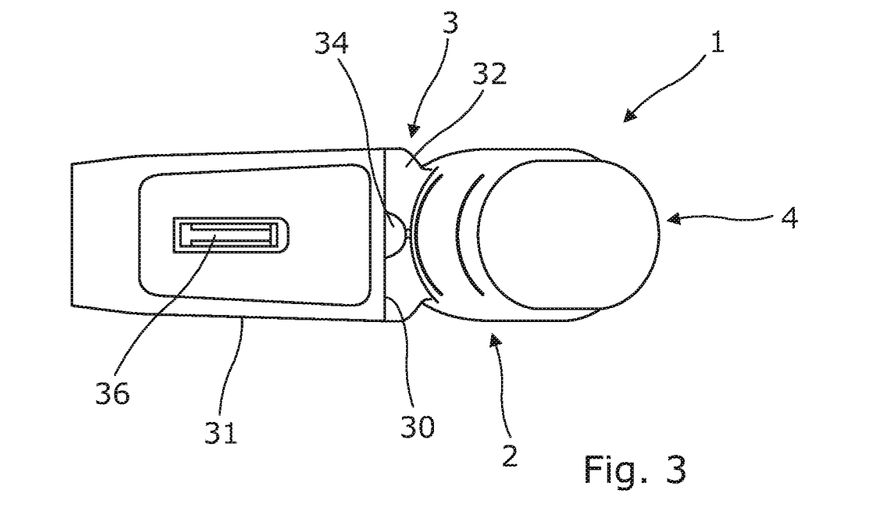
FIG. 3 shows a top view of the first embodiment of the present invention.

The body extension 3 comprises a tubular extension extending from the closed lower end 8 of the cylindrical portion 6 of the body 2. The tubular extension comprises a receiving portion 29 with an open end distal the body 2 for receiving the attachment end 30 of a spacer 31 in a press-fit arrangement. The tubular extension comprises a connecting portion 32 which connects the receiving portion 29 to the body 2. There is preferably a stepped join 33 between the receiving portion 29 and the connecting portion 32 which limits the extent to which the spacer 31 can be fitted onto the tubular extension so that the receiving portion 29 may be enclosed within the spacer 31 but the connecting portion 32 remains exposed.

Two air inlets 34, 34' are defined by opposing, aligned notches in the body extension 3 extending from the open end of the receiving portion 29 and through the connecting portion 32 to the sealing plate 28. The two air inlets are of equal size and each has an area of around 10 mm$^2$, 28.5 mm$^2$, 30 mm$^2$, 59 mm$^2$ or 66 mm$^2$—these areas provide air flow rates and back pressure values which match five commonly used PMDIs. It should be noted that the area of the air inlets is equivalent to the area of the notches in the connecting portion 32 of the tubular extension.

The sealing plate 28 is provided with a deviator 35 in alignment with the two air inlets 34, 34'. The deviator 35 acts prevent the two streams of the inhalation flow path entering through the two air inlets 34, 34' from buffeting each other and creating turbulence. The deviator 35 is a circular bump. The bump has a height such that it protrudes from the sealing plate by an amount that is around ⅓ of the length of the connecting portion 32 (i.e. from the sealing plate 28 to receiving portion 29) of the tubular extension.

The device further includes a counter (shown in FIGS. 8 and 9) for providing an audible indication of time elapsed since actuation of the air expulsion means 5.

The Figures show the device in combination with a spacer 31. This spacer includes a sound generator 36 which generates an audible tone when the correct air flow rate for drug delivery is achieved.

Accordingly, the user affixes the attachment end 30 of the spacer 31 to the body extension 3 and inhales until the tone indicating the correct flow rate is generated by the spacer 31. At that time, the user depresses the actuator 4 to activate the air expulsion means 5. The air expulsion means 5 acts to force air through the restricted air flow path thus generating an audible signal that is comparable to the sound generated by the propellant gases upon depression of a canister into the body of a PMDI. The user is then instructed to continue breathing in after hearing the audible signal generated by the device 1 for as long as they can whilst maintaining the tone generated by the spacer 31. Preferably, the counter will provide some indication of time elapsed and the user should aim to keep inhaling for at least five seconds after depression of the actuator 4/actuation of the air expulsion means 5. Accordingly, by using the device 1 of the present invention, especially in combination with the FLO-TONE pMDI attachment spacer 31, a user can learn to use a PMDI correctly by undergoing a realistic training experience where the actions of using the device and the sounds generated by the device accurately mimic those of a PMDI.

Figures 6, 7:
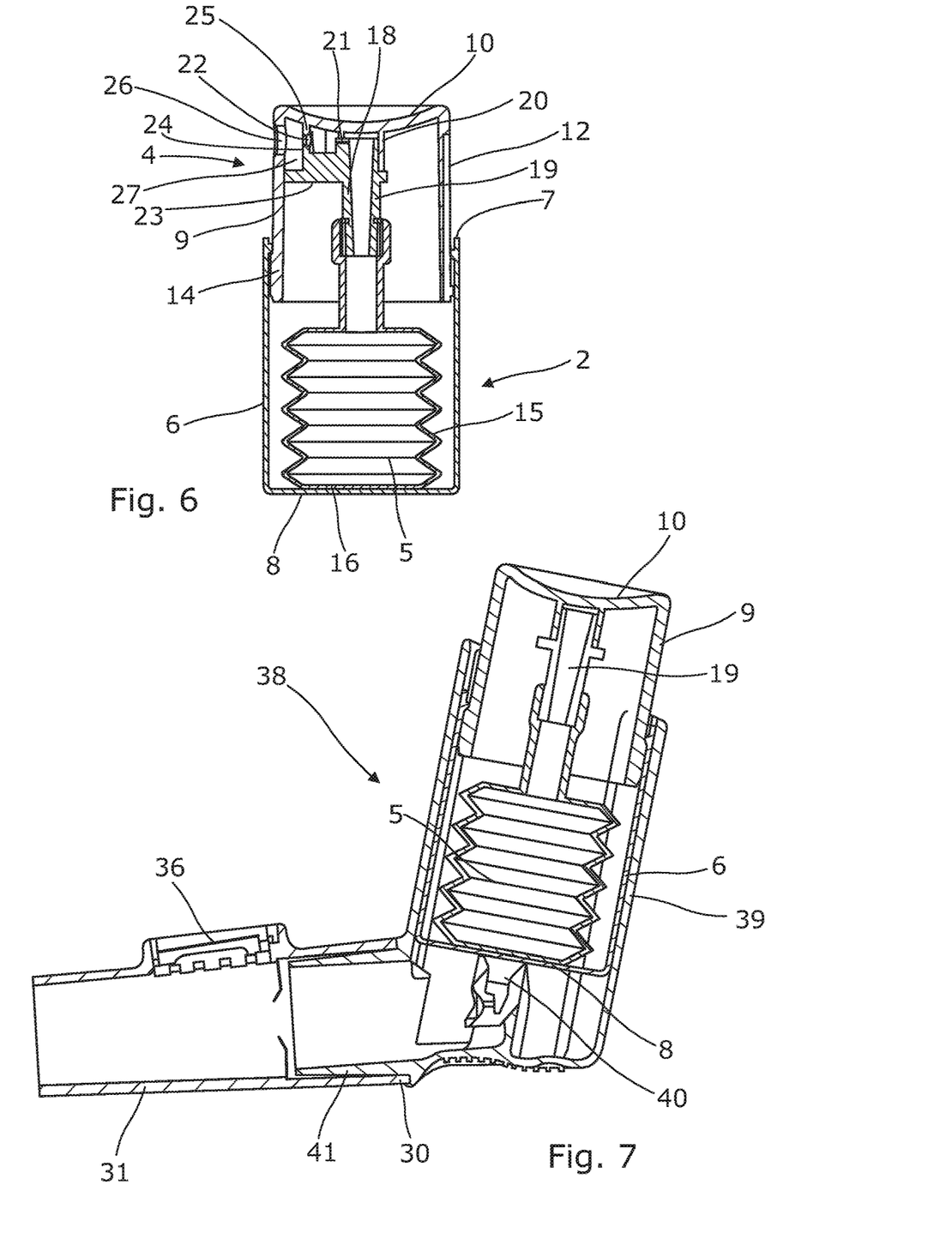
FIG. 6 shows a cross-sectional view through a second preferred embodiment.
FIG. 7 shows a cross-section view through the second preferred embodiment when in sit within a PMDI body.

FIGS. 6 and 7 show a second preferred embodiment of a training device for training a user to use a pressurised metered dose inhaler (PMDI). FIG. 7 shows the device in combination with an empty PMDI body with a FLO-TONE pMDI attachment spacer attached.

The device 1 comprises a body 2 and an actuator 4 for actuation of air expulsion means 5.

The body 2 has a cylindrical portion 6 having an open upper end 7 and a closed lower end 8.

The actuator 4 comprises a cylindrical element 9 having a closed upper end 10 and an open lower end 11 which is inserted into the open upper end 7 of the cylindrical portion 6 of the body 2 (the diameter of the actuator 4 being less that the diameter of the cylindrical portion 6 of the body 2.)

The cylindrical element 9 forms a sliding fit within the cylindrical portion 6 of the body 2 and depression of the actuator 4 into the body 2 effects actuation of the air expulsion means 5. The closed upper end 10 of the actuator 4 includes a depression for receiving a user's finger for depression of the actuator 4 into the body 2.

The actuator 4 comprises cooperation means for cooperating with the body to prevent rotational movement within the body and/or to prevent removal of the actuator from the body. The actuator cooperation means comprises a groove 12 which cooperates with a complementary ridge inside the body for preventing rotational movement of the actuator 4 within the body 2.

The actuator cooperation means additionally comprises an annular enlargement 14 of at least part of the rim of the open lower end 11 of the cylindrical element 9 of the actuator 4, the annular enlargement 14 for cooperating with lugs (not shown) on the inside of the walls of the cylindrical portion 6 of the body 2 for preventing removal of the actuator 4 from the body 2.

The air expulsion means 5 are for expelling air along an air flow path. The air expulsion means 5 comprises piston bellows having a cylindrical portion defined by corrugated walls 15 and a closed lower end 16. The volume of the cylindrical portion of the bellows is reducible by compression of the corrugated walls 15 upon actuation by depression of the actuator 4 into the body 2. As the volume of the bellows is decreased, air is expelled along the air flow path.

The closed lower end 8 of the cylindrical portion 6 of the body 2 is in abutment with the closed lower end 16 of the piston bellows.

The air expulsion means 5 and actuator 4 are connected by an insert 18 and movement (i.e. depression of the actuator 4) is transferred directly to the air expulsion means 5 through the insert 18. The insert 18 comprises a duct 19 defining the air flow path from the air expulsion means 5 to proximal the closed upper end 10 of the actuator 4. The duct 19 is received in a seat 20 provided on the inside of the closed upper end 10 of the actuator 4.

When the air flow path reaches the closed upper end 10 of the actuator 4, it is deflected through 90 degrees through an orifice 21 in the duct 19, the orifice 21 having a smaller cross-sectional area than the duct 19. The orifice 21 constitutes a first (upstream) restriction in the air flow path.

The air flow path further includes a second (downstream) orifice 22, the second orifice 22 having larger cross-sectional area than the first upstream orifice 21. The upstream orifice 21 is closer to the air expulsion means 5 than the downstream orifice 22.

Upon expulsion of air (from the air expulsion means 5) along the air flow path, the smaller upstream orifice 21 creates a high speed jet of air and the larger downstream orifice 22 creates a turbulent air flow which generates an audible signal.

Both the upstream and downstream orifices 21, 22 are defined by the insert 18 connecting the air expulsion means 5 and actuator 4. The first (upstream) orifice is provided in the duct 19 of the insert just after the 90 degree deflection of the air flow path. The insert 18 comprises a flange 23 extending from the duct 19 and supporting an upstanding plate 24, the upstanding plate 24 partially defining the downstream orifice 22 which is in alignment with and spaced from the upstream orifice 21. The upstanding plate 24 extends to a lug 25 extending down from the inside of the closed upper end 10 of the actuator 4. The lug 25 partially defines the upstream orifice 22.

The air flow path extends from the air expulsion means 5 to an outlet port 26 in the actuator 4. The downstream orifice 22 is proximal the outlet port 26 so that any damping by the body 2 and the actuator 4 of the audible signal generated by the air as it passes through the downstream orifice 22 is minimised.

To further increase the volume of the audible signal, a sound box 27 is provided in the air flow path, adjacent the outlet port 26. The air flow path passes through the sound box 27 after passing through the orifices 21, 22 and the sound box 27 acts to amplify the audible signal generated.

The sound box 27 is defined by the walls of cylindrical element of the actuator 4 surrounding the outlet port 26, the closed upper end 10 of the actuator 4, the flange 23 depending from the duct 19 of the insert (where the flange 23 extends up to the walls of cylindrical element of the actuator 4) and by inner walls (not shown) depending from the inside of the closed upper end 10 of the cylindrical element of the actuator 4, the inner walls extending downwards to the flange 23 and across to the walls of the cylindrical element of the actuator 4. The inner walls extend either side of the lug 25 which at least partly defines the second, upstream orifice 22.

The device further includes a counter (shown in FIGS. 8 and 9) for providing an audible indication of time elapsed since actuation of the air expulsion means 5.

FIG. 7 shows the device 1 within a PMDI body 38 in combination with a spacer 31. This spacer includes a sound generator 36 which generates an audible tone when the correct air flow rate for drug delivery is achieved.

Accordingly, the user inserts the device 1 into the cylindrical portion 39 of the PMDI body so that the closed lower end 8 of the cylindrical portion 6 of the body is in abutment with the valve seat 40. The user affixes the attachment end 30 of the spacer 31 to the PMDI mouthpiece 41 and inhales until the tone indicating the correct flow rate is generated by the spacer 31. At that time, the user depresses the actuator 4 to activate the air expulsion means 5. The air expulsion means 5 acts to force air through the restricted air flow path thus generating an audible signal that is comparable to the sound generated by the propellant gases upon depression of a canister into the PMDI body. The user is then instructed to continue breathing in after hearing the audible signal generated by the device 1 for as long as they can whilst maintaining the tone generated by the spacer 31. Preferably, the counter will provide some indication of time elapsed and the user should aim to keep inhaling for at least five seconds after depression of the actuator 4/actuation of the air expulsion means 5. Accordingly, by using the device 1 of the present invention, especially in combination with the FLO-TONE pMDI attachment spacer 31, a user can learn to use a PMDI correctly by undergoing a realistic training experience where the actions of using the device and the sounds generated by the device accurately mimic those of a PMDI.

Figure 8:
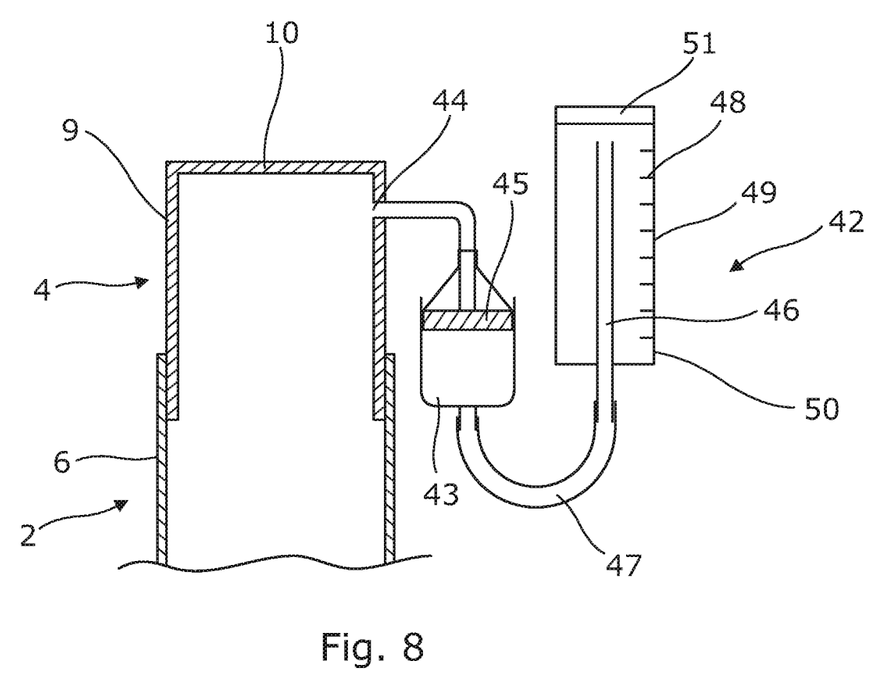
FIG. 8 shows a cross-section through a counter which may be used with the first or second embodiment.
Figure 9:
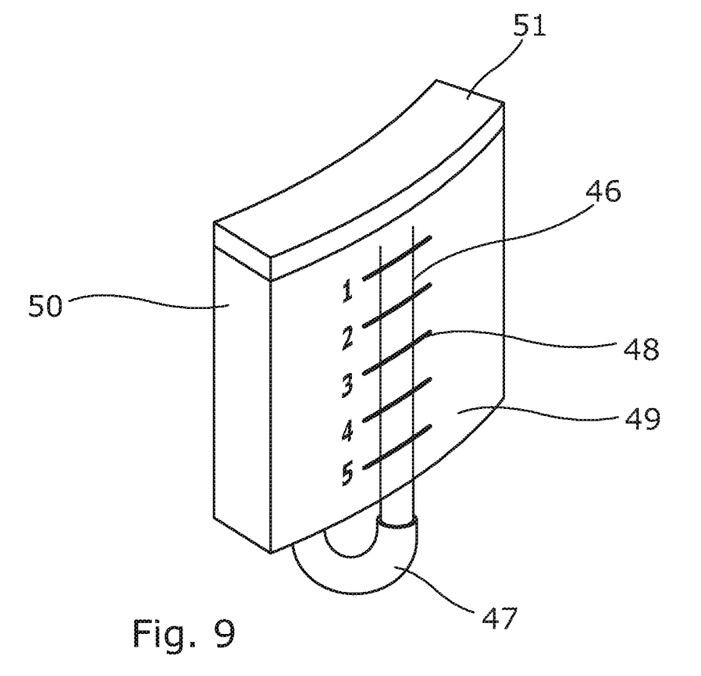
FIG. 9 shows a front perspective view of the display of the counter.

FIGS. 8 and 9 show a counter 42 for use with the first or second embodiment for providing a visual indication of the time elapsed since actuation of the air expulsion means. The counter 42 comprises a liquid-filled reservoir 43 connected to a second air flow path (not shown), the second air flow path extending from the bellows to a second outlet 44 in the actuator. The second outlet 44 is connected to a plunger 45 which seals the liquid-filled reservoir 43. The liquid-filled reservoir is connected to an upstanding capillary tube 46 by a U-tube 47. The capillary tube 46 is visible to the user as they use the device through graduations 48 on a front screen 49 of a display 50 sealed with a fluid-impermeable seal 51. As the actuator 4 is depressed into the cylindrical portion of the body 6, air is expelled along the second air flow path to the second outlet 44 and this actuates the plunger 45 which increases the pressure in the liquid-filled reservoir 43. This causes the liquid to rise within the upstanding tube 46. The viscosity of the liquid in the reservoir is selected such that, after rising within the tube 46, it recedes back into the reservoir 43 (and the U-tube 47) at a predetermined rate. The predetermined rate is such that it recedes back into the reservoir over a time period of around 5 seconds. The graduations 48 on the display indicate to the user the rate at which the liquid is receding allowing them to determine the length of time for which they have been inhaling since actuation of the air expulsion means 5.

Figure 10A:
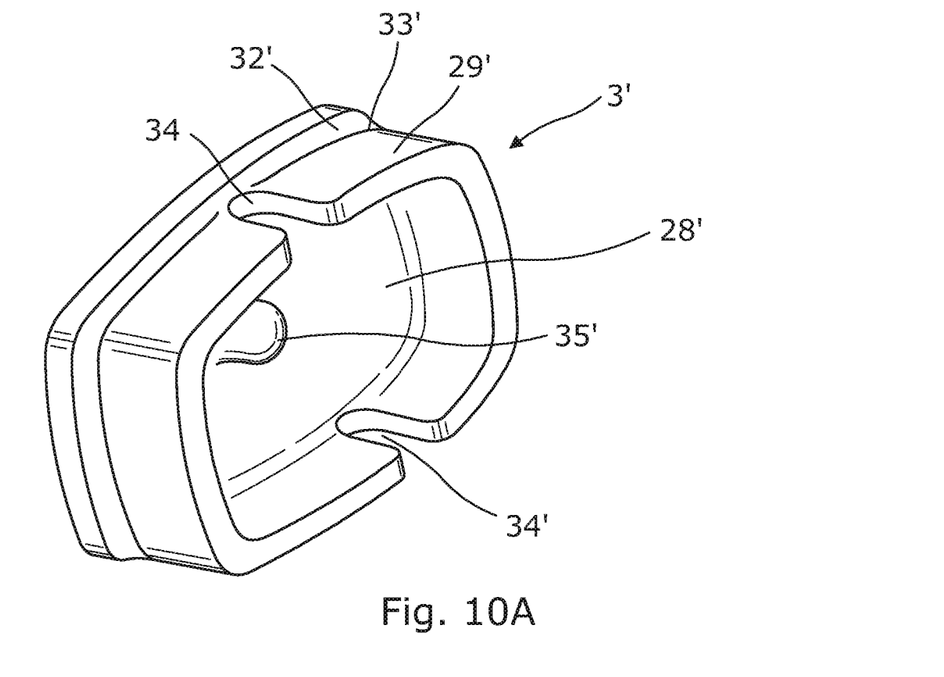
FIGS. 10A and 10B show a front perspective and rear respective view of a replaceable body extension.
Figure 10B:
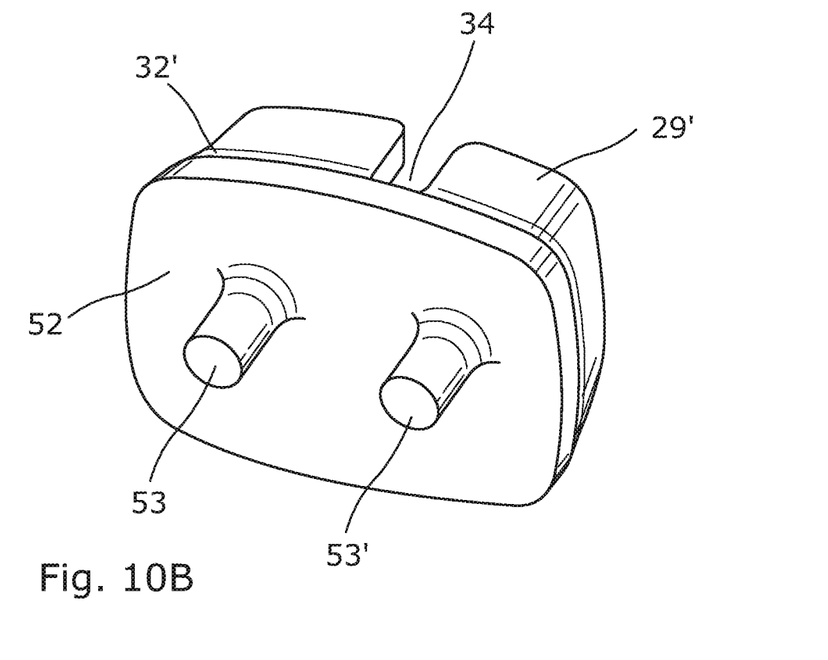

FIGS. 1 to 5 show an embodiment with an integral body extension 3. Alternative embodiments may be identical to that shown in FIGS. 1 to 5 but with a detachable/replaceable body extension 3' as shown in FIGS. 10A and 10B.

The detachable body extension 3' comprises a sealing plate 28' which has a smooth surface and forms a smooth join with the walls of the body extension 3 i.e. there are no abrupt deflections between the sealing plate 28' and the walls of the body extension 3'.

The body extension 3' comprises a tubular extension having a receiving portion 29' with an open end for receiving the attachment end 30 of a spacer 31 in a press-fit arrangement. The tubular extension further comprises a connecting portion 32'. There is preferably a stepped join 33' between the receiving portion 29' and the connecting portion 32' which limits the extent to which the spacer 31 can be fitted onto the tubular extension so that the receiving portion 29' may be enclosed within the spacer 31 but the connecting portion 32' remains exposed.

The rear surface 52 of the sealing plate 28' has connection means comprising 2 projections 53, 53' which are insertable into two holes (not shown) at the lower end of the cylindrical portion 6 of the body 2 to form a device which resembles the shape of a PMDI. The body extension 3' is releasably attachable to the body 2 to that, after use, it can be removed and discarded or cleaned. Alternatively, the connection means comprising two projections 53, 53' are insertable into the expansion chamber/actuator nozzle region of an empty PMDI body.

Two air inlets 34, 34' are defined by opposing, aligned notches in the body extension 3' extending from the open end of the receiving portion 29' and through the connecting portion 32' to the sealing plate 28'. The two air inlets are of equal size and each has an area of around 10 mm$^2$, 28.5 mm$^2$, 30 mm$^2$, 59 mm$^2$ or 66 mm$^2$—these areas provide air flow rates and back pressure values which match five commonly used PMDIs. It should be noted that the area of the air inlets is equivalent to the area of the notches in the connecting portion 32' of the tubular extension.

The sealing plate 28' is provided with a deviator 35' in alignment with the two air inlets 34, 34'. The deviator 35' acts prevent the two streams of the inhalation flow path entering through the two air inlets 34, 34' from buffeting each other and creating turbulence. The deviator 35' is a circular bump. The bump has a height such that it protrudes from the sealing plate by an amount that is around ⅓ of the length of the connecting portion 32' (i.e. from the sealing plate 28' to receiving portion 29') of the tubular extension.

The invention claimed is:

1. A training device for training a user to use a pressurized metered dose inhaler, the device comprising:
    a body;
    an air expulsion means for expelling air without a release of any propellant gas along an air flow path, wherein the air expulsion means comprises a body element which has a variable volume or comprises a body element which has a variable volume portion such that, as the volume of the variable volume body element/portion is reduced, air is expelled from the variable volume body element/portion along the air flow path; and
    an actuator for actuation of the air expulsion means;
    wherein the air flow path comprises a restriction such that upon expulsion of air along the air flow path, an audible signal is generated; and
    wherein the air flow path extends from the air expulsion means to an outlet port in the actuator, such that when the actuator is actuated by the user the air is expelled out of the outlet port and away from the user's mouth.

2. The device according to claim 1, wherein the actuator forms a sliding fit within the body and depression of the actuator into the body effects actuation of the air expulsion means.

3. The device according to claim 1, wherein the body has a tubular portion having an open upper end and a closed lower end and wherein the actuator comprises a tubular element having a closed upper end and an open lower end which is inserted into the open upper end of the tubular portion of the body.

4. The device according to claim 1, wherein the variable volume body/portion has a wall portion which is deformable upon actuation of the actuator, or the variable body/portion is entirely defined by walls which are deformable upon actuation of the actuator.

5. The device according to claim 4, wherein the device further comprises a resistance member for abutment with the variable volume body/portion such that upon actuation of the air expulsion means, the variable volume body/portion is pressed against the resistance member thus causing deformation of the deformable wall portion/walls.

6. The device according to claim 1, wherein the air expulsion means comprises bellows.

7. The device according to claim 1, wherein the restriction in the air flow path is proximal to the outlet port.

8. The device according to claim 7, wherein the device further comprises a sound box in the air flow path adjacent the outlet port.

9. The device according to claim 1, wherein the restriction in the air flow path is an orifice having a reduced cross-sectional area.

10. The device according to claim 1, wherein the air flow path comprises a plurality of restrictions.

11. The device according to claim 10, wherein the air flow path comprises an upstream orifice having a smaller cross-sectional area than the air flow path and a downstream orifice having larger cross-sectional area than the upstream orifice.

12. The device according to claim 3, wherein the device further comprises a body extension and a sealing plate is provided between the body extension and the tubular portion of the body, and wherein the device further comprises at least one air inlet defined at least partly by the body extension.

13. The device according to claim 12, comprising at least one notch in the body extension, the at least one notch extending from an open end of the body extension towards the body.

14. The device according to claim 13, further comprising two opposed notches in the body extension.

15. The device according to claim 12, wherein the body extension comprises a tubular extension extending from the closed lower end of the tubular portion of the body, the tubular extension comprising a receiving portion with an open end distal the body for receiving the attachment end of a spacer, the tubular extension further comprising a connecting portion between the receiving portion and the body, wherein there is a stepped join/ridge or an intermediate portion having a plurality of stop points between the receiving portion and the connecting portion.

16. The device according to claim 15, further comprising two opposed notches, aligned either side of the tubular extension, wherein the sealing plate comprises a deviator in alignment with the two notches.

17. The device according to claim 16, wherein the tubular extension comprises a stepped join/ridge between the connecting portion and the receiving portion and the total area of each notch in the connecting portion is between 20 and 150 mm$^2$.

18. The device according to claim 16, wherein the tubular extension comprises an intermediate portion having at least a first stop point proximal the connecting portion and a second stop point proximal the receiving portion and the first total area of each notch defined by the connecting portion and the intermediate portion between the connecting portion and the first stop point is smaller than the second total area of each notch defined by the connecting portion and the intermediate portion between the connecting portion and the second stop point and wherein both the first total area and the second total area are between 20 and 150 mm$^2$.

19. The device according to claim 1, further comprising a counter for providing an indication of time elapsed since actuation of the air expulsion means.

\* \* \* \* \*